(12) United States Patent
Furukawa et al.

(10) Patent No.: US 8,846,840 B2
(45) Date of Patent: Sep. 30, 2014

(54) ADAMANTYL (METH)ACRYLIC MONOMER AND (METH)ACRYLIC POLYMER CONTAINING THE SAME AS REPEATING UNIT

(75) Inventors: Kikuo Furukawa, Tokyo (JP); Toshiharu Yamashita, Mie (JP); Yoshio Nishimura, Mie (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/637,764

(22) PCT Filed: Mar. 29, 2011

(86) PCT No.: PCT/JP2011/057729
§ 371 (c)(1),
(2), (4) Date: Sep. 27, 2012

(87) PCT Pub. No.: WO2011/125630
PCT Pub. Date: Oct. 13, 2011

(65) Prior Publication Data
US 2013/0023638 A1    Jan. 24, 2013

(30) Foreign Application Priority Data
Apr. 1, 2010   (JP) .................................. 2010-085038

(51) Int. Cl.
| | |
|---|---|
| *C08F 220/18* | (2006.01) |
| *C08F 220/28* | (2006.01) |
| *C07C 69/54* | (2006.01) |
| *C07C 67/48* | (2006.01) |
| *C07C 67/08* | (2006.01) |
| *G03F 7/039* | (2006.01) |
| *C08F 4/04* | (2006.01) |

(52) U.S. Cl.
CPC .............. *C07C 69/54* (2013.01); *C07C 2103/74* (2013.01); *C08F 220/28* (2013.01); *C08F 220/18* (2013.01); *G03F 7/0397* (2013.01)
USPC .............. 526/282; 526/75; 560/218; 560/220

(58) Field of Classification Search
USPC .............................. 526/75, 282; 560/218, 220
See application file for complete search history.

(56) References Cited

U.S. PATENT DOCUMENTS 6,495,306 B2 * 12/2002 Uetani et al. ............... 430/270.1
2001/0026901 A1   10/2001 Maeda et al.

FOREIGN PATENT DOCUMENTS

| JP | 2881969 | 4/1999 |
|---|---|---|
| JP | 3042618 | 3/2000 |
| JP | 2001-192356 | 7/2001 |
| JP | 2002-145955 | 5/2002 |
| JP | 2002-226436 | 8/2002 |
| JP | 2002-273774 | 9/2002 |
| JP | 2002-293774 | 10/2002 |
| JP | 2004-323704 | 11/2004 |
| JP | 2009-091334 | 4/2009 |
| JP | 2009-143827 | 7/2009 |

OTHER PUBLICATIONS

Machine translation of JP 2009-143827A (Jul. 2009).*
Machine translation of JP 2009-091334A (Apr. 2009).*
Machine translation of JP 2004-323704A (Nov. 2004).*
Naomi Shida et al., "Advance Materials for 193-nm Resists", Journal of Photopolymer Science and Technology, 2000, pp. 601-606, vol. 13, No. 4.
Search report from International Application No. PCT/JP2011/057729, mail date is May 17, 2011.

* cited by examiner

*Primary Examiner* — Fred M Teskin
(74) *Attorney, Agent, or Firm* — Greenblum & Bernstein, P.L.C.

(57) ABSTRACT

Provided according to the present invention are an adamantyl (meth)acrylate represented by formula (1), having a formazin standard turbidity of less than 1.7 NTU (Nephelometric Turbidity Unit) in methylethylketone or tetrahydrofuran, and also a (meth)acrylic copolymer comprising the adamantyl (meth)acrylate as a repeating unit:

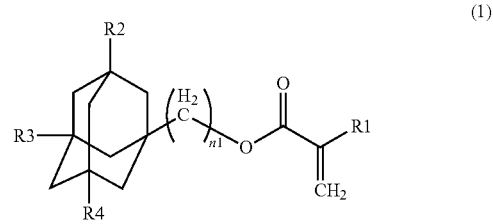

(1)

(in the formula, R1 represents hydrogen or a methyl group; R2 through R4 each independently represent a hydrogen atom, a hydroxyl group, an alkyl group having a carbon number of 1 to 3, an aryl group, an alkoxy group, an aryloxy group, a halogen group, an alkyl halide group, or a hydroxyalkyl group; and n1 represents 0 or 1).

8 Claims, No Drawings

ADAMANTYL (METH)ACRYLIC MONOMER AND (METH)ACRYLIC POLYMER CONTAINING THE SAME AS REPEATING UNIT

TECHNICAL FIELD

The present invention relates an adamantyl (meth)acrylate and a copolymer containing the same as a repeating unit, which are usable for a resist for producing a semiconductor device.

BACKGROUND ART

For producing a semiconductor device, a technique called "photolithography" of transferring a circuit pattern onto a wafer by use of a photosensitive resin is used as a technology of forming a fine pattern. Especially by the cutting-edge technology of photolithography, an ArF excimer laser having a wavelength of 193 nm is used, and a copolymer containing an alicyclic monomer having a crosslinked structure in a repeating unit is used as a resist in consideration of light transmittance and anti-etching characteristic (see, for example, Patent Documents 1 through 3). Among alicyclic monomers, an adamantane derivative has a stable and firm structure, is highly symmetrical structurally, and can provide various properties depending on the functional group introduced, and therefore, is widely used.

Recently, the densities of semiconductor devices are becoming increasingly higher. In order to form higher density patterns, a copolymer usable for a resist which can reduce the amount of impurities to the minimum possible level and thus can improve the production yield of the semiconductor devices are desired. Impurities contained in a copolymer include polymerizable impurities which are mixed as a contaminant during production thereof or derived from a monomer as a material of the copolymer. Among such impurities, monomer- or esterification agent-derived homopolymers or oligomers reduce sensitivity or resolution during the photolithography process, or reduce the yield rate, for example, increase the line edge roughness (LER). Such polymerizable impurities also reduce the solubility of the copolymer in a photoresist solvent. This causes defects of a lithographic pattern, such as insufficient spin-coating, increase of developing defects after exposure/development or the like. Such defects of the lithographic pattern directly influence the production yield rate of the semiconductor devices. For these reasons, it is considered not to preferable to use a copolymer containing polymerizable impurities as a material for producing the photoresist. Various proposals have been made in order to reduce the amount of the polymerizable impurities (see, for example, Patent Document 4). However, the polymerizable impurities brought into the copolymer from the monomer used cannot be completely removed on or after the stage of polymer production. Therefore, it is required to reinforce the quality control on the stage of monomer production. In addition, gel permeation chromatography (GPC) analysis, which is used for analysis of the polymerizable impurities, cannot accurately measure the concentration of, and therefore cannot properly control, the polymerizable impurities containing an adamantyl group because such polymerizable impurities have a low solubility in a solvent used in the gel permeation chromatography analysis. In such circumstances, it has been desired to develop a monomer having a further improved quality and a high purity copolymer suitable for production of the next-generation semiconductor devices.

CITATION LIST

Patent Literature

Patent Document 1: Japanese Patent No. 2881969
Patent Document 2: Japanese Patent No. 3042618
Patent Document 3: Japanese Laid-Open Patent Publication No. 2002-145955
Patent Document 4: Japanese Laid-Open Patent Publication No. 2004-323704

SUMMARY OF INVENTION

Technical Problem

The present invention made in light of the above-described problems has an object of providing an adamantyl (meth)acrylate (hereinafter, acrylate and methacrylate will be collectively referred to as "(meth)acrylate") which has high transparency and etching resistance and thus is usable as a resist material for lithography exposed upon a KrF or ArF excimer laser, electron beams, X-rays, or extreme ultraviolet (EUV; wavelength: 13.5 nm), and also has superb transparency and resolution and thus is technologically preferable for improving the density of a semiconductor device, which will be more and more raised in the future; and also of providing a (meth)acrylic copolymer containing the adamantyl (meth)acrylate as a repeating unit.

Solution to Problem

As a result of active studies made in an attempt to solve the above-described problems, the present inventors found the following regarding an adamantyl (meth)acrylate, which is a material of a (meth)acrylic copolymer usable for a photoresist. When an adamantyl (meth)acrylate having a formazin standard turbidity of less than 1.7 NTU when being dissolved or diluted in an organic solvent (methylethylketone or tetrahydrofuran) for a reaction or polymerization is used as a repeating unit of a (meth)acrylic copolymer, the obtained (meth)acrylic copolymer exhibits superb line edge roughness and resolution in a lithography process for forming a pattern on a silicon wafer. This occurs even the above-described adamantyl (meth)acrylate does not show a distinct difference from other types of adamantyl (meth)acrylates by GPC analysis. As a result of such a finding, the present inventors completed the present invention. This result shows that the obtained (meth)acrylic copolymer has a superb lithography performance because the sensitivity, resolution, and line edge roughness have a trade-off relationship in general.

The above-described problems can be solved by the present invention described below.

<1> An adamantyl (meth)acrylate represented by formula (1), having a formazin standard turbidity of less than 1.7 NTU when being dissolved or diluted in methylethylketone or tetrahydrofuran:

[Chemical Formula 1]

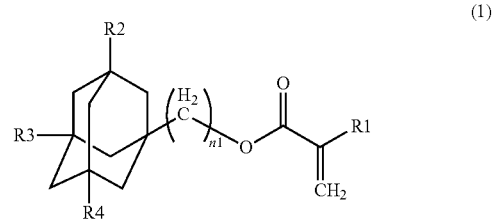

(1)

(in the formula, R1 represents hydrogen or a methyl group; R2 through R4 each independently represent a hydrogen atom, a hydroxyl group, an alkyl group having a carbon number of 1 to 3, an aryl group, an alkoxy group, an aryloxy group, a halogen group, an alkyl halide group, or a hydroxyalkyl group; and n1 represents 0 or 1).

<2> The adamantyl (meth)acrylate according to <1> above, which is selected from the group consisting of 1-adamantyl (meth)acrylate, 3-hydroxy-1-adamantyl (meth)acrylate, 3,5-dihydroxy-1-adamantyl (meth)acrylate, 3,5,7-trihydroxy-1-adamantyl (meth)acrylate, 3,5-dimethyl-1-adamantyl (meth)acrylate, 5,7-dimethyl-3-hydroxy-1-adamantyl (meth)acrylate, 5-methoxy-3-hydroxy-1-adamantyl (meth)acrylate, 5-ethoxy-3-hydroxy-1-adamantyl (meth)acrylate, (meth)acryloyloxy-(1-adamantyl)methane, and (meth)acryloyloxy-(1-(3-hydroxymethyl)adamantyl)methane.

<3> A polymer, comprising the adamantyl (meth)acrylate according to <1> or <2> above as a repeating unit.

<4> A method for producing the adamantyl (meth)acrylate according to <1> above, the method comprising the steps of causing a dehydration esterification reaction of an adamantanol represented by formula (2) and a (meth)acrylic acid in the presence of an acid catalyst; and performing refinement while supplying oxygen-containing gas in the presence of a phenol-based and/or quinone-based polymerization inhibitor in post-treatment performed after the dehydration esterification reaction:

[Chemical Formula 2]

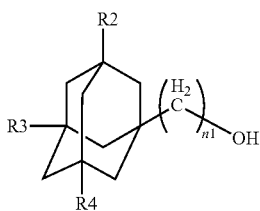

(2)

(in the formula, R2 through R4 may be the same as, or different from each other, and each represent a hydrogen atom, a hydroxyl group, an alkyl group having a carbon number of 1 to 3, an aryl group, an alkoxy group, an aryloxy group, a halogen group, an alkyl halide group, or a hydroxyalkyl group; and n1 represents 0 or 1).

<5> The method according to <4> above, further comprising the step of performing precise filtration in the post-treatment performed after the dehydration esterification reaction.

<6> The method according to <4> or <5> above, wherein the adamantyl (meth)acrylate is selected from the group consisting of 1-adamantyl (meth)acrylate, 3-hydroxy-1-adamantyl (meth)acrylate, 3,5-dihydroxy-1-adamantyl (meth)acrylate, 3,5,7-trihydroxy-1-adamantyl (meth)acrylate, 3,5-dimethyl-1-adamantyl (meth)acrylate, 5,7-dimethyl-3-hydroxy-1-adamantyl (meth)acrylate, 5-methoxy-3-hydroxy-1-adamantyl (meth)acrylate, 5-ethoxy-3-hydroxy-1-adamantyl (meth)acrylate, (meth)acryloyloxy-(1-adamantyl)methane, and (meth)acryloyloxy-(1-(3-hydroxymethyl)adamantyl)methane.

<7> The method according to any one of <4> through <6> above, wherein the gas used in the step of performing the precise filtration has an oxygen concentration of 0.05 to 10% by volume.

<8> The method according to any one of <4> through <7> above, wherein the gas used in the step of performing the precise filtration is supplied in an amount of 0.005 to 0.3 L/min. with respect to 1 mol of the adamantanol.

<9> A (meth)acrylic copolymer obtained as a result of copolymerization of the adamantyl (meth)acrylate according to <1> above and at least one compound selected from the group consisting of compounds represented by formula (3), formula (4), formula (5) and formula (6), wherein the adamantyl (meth)acrylate is contained at a content of 5 to 40% by weight:

[Chemical Formula 3]

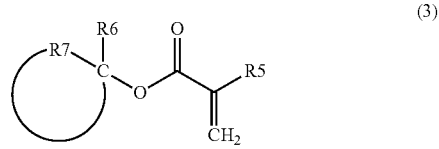

(3)

(in the formula, R5 represents hydrogen or a methyl group; R6 represents an alkyl group having a carbon number of 1 to 4; and R7 represents a cycloalkyl group or an alicyclic alkyl group having a carbon number of 5 to 20);

[Chemical Formula 4]

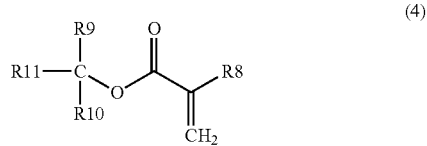

(4)

(in the formula, R8 represents hydrogen or a methyl group; R9 and R10 may be the same as, or different from each other, and each represent an alkyl group having a carbon number of 1 to 4; and R11 represents a cycloalkyl group or an alicyclic alkyl group having a carbon number of 5 to 20);

[Chemical Formula 5]

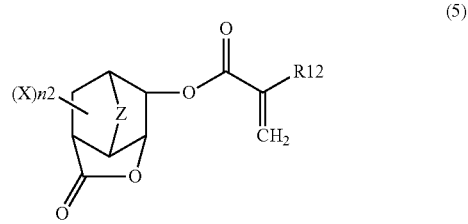

(5)

(in the formula, R12 represents hydrogen or a methyl group; Z represents methylene (—CH$_2$—) or oxa (—O—); Xs may be the same as, or different from, each other, and each represent a hydroxyl group, a halogen group, a nitrile group, a carboxylic acid group, or an alkoxycarbonyl group having a carbon number of 1 to 4, or an alkoxide group having a carbon number of 1 to 4; and n2 represents an integer of 0 to 2); and

[Chemical Formula 6]

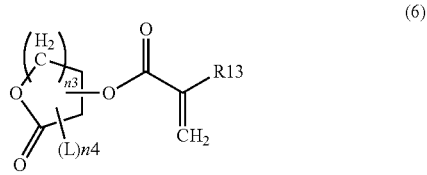

(6)

(in the formula, R13 represents hydrogen or a methyl group; n3 represents an integer of 1 to 3; L represents a methyl group, an ethyl group, a hydroxyl group, or a halogen group; and n4 represents an integer of 0 to 2).

Advantageous Effects of Invention

A (meth)acrylic copolymer containing an adamantyl (meth)acrylate according to a preferable embodiment of the present invention as a repeating unit exhibits basic performances as a photoresist such as high transparency, etching resistance and the like, and also exhibits superb sensitivity and resolution when a silicon wafer is processed, for example, when an independent pattern, a line-and-space pattern, a contact hole or the like is formed. Therefore, the adamantyl (meth)acrylate and the (meth)acrylic copolymer according to the present invention can contribute to the improvement of the densities of semiconductor integrated circuits, which is more and more required in the future.

DESCRIPTION OF EMBODIMENTS

In the present invention, the "turbidity" is one standard for measuring the amount of polymerizable impurities. The turbidity indicates how turbid the solution or the like is, and is measured by a nephelometric analysis. In general, nephelometric analysis is an analysis of quantifying a substance by measuring light absorbed by a suspension (described in, for example, "Kagaku Daijiten" published by Kyoritsu Shuppan Co., Ltd.). The method of measuring the turbidity is described in detail in JIS K0801.

The "formazin standard turbidity" described in this specification is defined as a numerical value obtained by dissolving or diluting 10 parts by weight of adamantyl (meth)acrylate in 100 parts by weight of solvent at room temperature to obtain a sample for measurement and then measuring the sample.

The formazin standard turbidity is measured by a turbidimeter. The turbidity is measured on the basis of the formazin standard solution. A StablCal standard solution is used to create a calibration curve. The measurement is performed on the above-described sample obtained by dissolving or diluting the adamantyl (meth)acrylate in a solvent.

According to the present invention, as a solvent for dissolving or diluting an adamantyl (meth)acrylate for measuring the formazin standard turbidity, methylethylketone or tetrahydrofuran is used. In these solvents, an adamantyl (meth)acrylate has a high solubility and polymerizable impurities have a low solubility. When any of these solvents is used, the value of the formazin standard turbidity is well correlated with performance of a photoresist produced using a (meth)acrylic copolymer synthesized by use of an adamantyl (meth)acrylate; specifically, is well correlated with, for example, line edge roughness (LER) derived from the polymerizable impurities, insufficient spin-coating, developing defects or the like of the photoresist. For these reasons, the above-described solvents are preferable.

Specific examples of the adamantyl (meth)acrylate represented by formula (1) include 1-adamantyl (meth)acrylate, 3-hydroxy-1-adamantyl (meth)acrylate, 3,5-dihydroxy-1-adamantyl (meth)acrylate, 3,5,7-trihydroxy-1-adamantyl (meth)acrylate, 3,5-dimethyl-1-adamantyl (meth)acrylate, 5,7-dimethyl-3-hydroxy-1-adamantyl (meth)acrylate, 5-methoxy-3-hydroxy-1-adamantyl (meth)acrylate, 5-ethoxy-3-hydroxy-1-adamantyl (meth)acrylate, (meth)acryloyloxy-(1-adamantyl)methane, (meth)acryloyloxy-(1-(3-hydroxymethyl)adamantyl)methane, and the like.

Now, a method for producing an adamantyl (meth)acrylate as described above will be described. In general, the adamantyl (meth)acrylate is produced from an adamantanol represented by formula (2) and a compound of (meth)acrylic acid. Specific methods include: a method of performing dehydration esterification with (meth)acrylic acid in the presence of an acid catalyst; a method of reacting acid halide or (meth)acrylic acid anhydride with a hydroxyl group; a method of using an ester such as methyl acrylate, methyl methacrylate or the like as a compound of a (meth)acrylic acid and removing the corresponding alcohol (methanol in the case of a methoxy group, ethanol in the case of an ethoxy group) outside the reaction system by distillation or the like; a method of putting a hydroxyl group of an adamantanol into an alcolate by use of an alkaline metal such as lithium, sodium or the like, an alkyl lithium such as butyl lithium or the like, a Grignard's reagent such as ethylmagnesium bromide or the like, and then performing an esterification reaction; and the like. A suitable method may be selected in accordance with a desired process, facilities or the like.

[Chemical Formula 7]

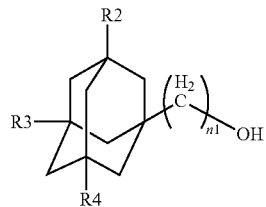

(2)

(In the formula, R2 through R4 may be the same as, or different from each other, and each represent a hydrogen atom, a hydroxyl group, an alkyl group having a carbon number of 1 to 3, an aryl group, an alkoxy group, an aryloxy group, a halogen group, an alkyl halide group, or a hydroxyalkyl group; and n1 represents 0 or 1.)

Examples of the adamantanol described above include 1-adamantanol, 1,3-adamantanediol, 1,3,5-adamantanetriol, 1,3,5,7-adamantanetetraol, 3,5-dimethyl-1-adamantanol, 5,7-dimethyl-1,3-adamantanediol, 5-methoxy-1,3-adamantanediol, 5-ethoxy-1,3-adamantanediol, 1-adamantanemethanol, 1,3-adamantanedimethanol, and the like. These adamantanols may contain a substituent.

A (meth)acrylic acid may be a methacrylic acid or an acrylic acid. The amount of the (meth)acrylic acid to be used is 0.5 to 100 equivalents, preferably 0.8 to 10 equivalents, more preferably 1 to 3 equivalents, with respect to the material (where the amount of the necessary (meth)acryloyloxy group is 1 equivalent). When the amount is smaller than such a range, the yield is decreased. An amount larger than such a range is not preferable because the excessively used amount needs to be treated, or a polymer such as an oligomer or the like is generated.

In the case where the method of promoting dehydration esterification by use of an acid catalyst is used, there is no specific limitation on the acid catalyst to be used as long as the acid catalyst is a strong acid which allows the dehydration reaction to proceed. In general, an inorganic acid such as sulfuric acid, phosphoric acid or the like, or an organic acid such as p-toluenesulfonic acid, benzenesulfonic acid, cresolsulfonic acid or the like is preferably used. The amount of the catalyst is 0.005 to 1.0 mol, preferably 0.01 to 0.1 mol, with respect to 1 mol of the adamantanol represented by formula (2). When the amount is smaller such a range, the reaction rate is decreased; whereas when the amount is larger than such a range, the selectivity of the adamantyl (meth)acrylate represented by formula (1) is decreased. According to this method, water generated as a secondary product during the reaction is removed outside the reaction system by azeotrope with the organic solvent used or a dehydration agent. As a result, the reaction is promoted and thus can be finished in a short time. As a specific method for removing the generated water, it is common to separate the moisture generated as the reaction proceeds from the reaction solvent by use of a Dean-Stark water separator and return only the reaction solvent to the reactor. The reaction can be allowed to proceed while the reaction solvent is returned to the reactor continuously or in batches. Methods for returning the reaction solvent to the reactor include: a method of returning the overflown part of the reaction solvent by gravity; a method of using the solution transportation by a pump or the like; etc. There is no specific limitation on the method for returning the reaction solvent. A distillation tower may be installed in the reactor to improve the efficiency of separating the reaction solvent from the water. As a dehydration agent, a known substance is usable such as concentrated sulfuric acid, boron trifluoride etherate, anhydrous trifluoroacetic acid, dicyclohexylcarbodiimide, 2-halobenzothiazoliumfluoroborate, 2-halogenized pyridinium salt, triphenylphosphine/carbon tetrachloride, thionyl chloride/basic compound, or the like.

A preferable reaction solvent usable for dehydration esterification is an organic solvent which has a low compatibility with water, has a high compatibility with an adamantanol represented by formula (2) and an adamantyl (meth)acrylate represented by formula (1), and is inactive to reaction. In order to remove the water generated as a secondary product during the reaction, it is preferable to use a solvent which causes azeotrope with water. Examples of such an organic solvent include aliphatic hydrocarbons having a carbon number of 6 to 10 such as hexane, heptane, octane, nonane, decane, and the like; alicyclic hydrocarbons having a carbon number of 6 to 10 such as cyclohexane, methylcyclohexane, dimethylcyclohexane, ethylcyclohexane, and the like; and aromatic hydrocarbons such as benzene, toluene, xylene, ethylbenzene, cumene, mesitylene, pseudocumene and the like. Usable dehydration agents include nitriles such as acetonitrile, benzonitrile, and the like; amides such as formamide, acetamide, dimethylformamide, dimethyacetamide, and the like; aliphatic hydrocarbons such as hexane, octane, and the like; aromatic hydrocarbons such as benzene and the like; hydrocarbon halide, nitro compounds, esters such as ethyl acetate, and the like; ethers such as diethylether, diisopropylether, tetrahydrofuran, dioxane, and the like; etc. These solvents may be used independently or in a mixture of two or more. The amount of the solvent is 0.1 to 20 parts by weight, preferably 1 to 10 parts by weight, with respect to 1 part by weight of the material. The reaction temperature is preferably 60 to 150° C. When the reaction temperature is lower than the 60° C., the reaction rate is significantly decreased; whereas when the reaction temperature is higher than 150° C., the selectivity of the adamantyl (meth)acrylate represented by formula (1) is decreased. The reaction temperature is basically determined by the azeotrope temperature of the organic solvent used and water at normal pressure, but may be adjusted by decreasing or increasing the reaction pressure.

The reaction step of producing the adamantyl (meth)acrylate represented by formula (1) may be performed under normal pressure, reduced pressure, or increased pressure, and may be performed by a known method such as a batch system, a semi-batch system, a continuous system or the like. The material quality of the reactor, the capacity of reaction or any other necessary reaction condition may be optionally selected in accordance with the feature of each type of esterification reaction.

It is preferable that a polymerization inhibitor is optionally incorporated for the esterification reaction, for the following reason. By incorporating a polymerization inhibitor, generation of a homopolymer or oligomer, which is one factor deteriorating the formazin standard turbidity, can be suppressed on the stage of the reaction. A common polymerization inhibitor is usable with no specific limitation. Usable polymerization inhibitors include quinones such as hydroxyquino line, hydroquinone, methylhydroquinone, p-benzoquinone, hydroquinonemonomethylether, and the like; phenols such as methoxyphenol, 2,4-dimethyl-6-t-butylphenol, catechol, 3-s-butylcatechol, 2,2-methylenebis-(6-t-butyl-4-methylphenol), and the like; nitroso compounds such as 2,2,6,6-tetramethyl-4-hydroxypiperidine-1-oxyl, N-nitrosophenylhydroxylamineammonium salt, N-nitrosophenylhydroxylaminealuminum salt, N-nitroso-N-(1-naphthyl)hydroxylamineammonium salt, N-nitrosodiphenylamine, N-nitroso-N-methylaniline, nitrosonaphthol, p-nitrosophenol, N,N'-dimethyl-p-nitro so aniline, and the like; amines such as N,N'-diphenyl-p-phenylenediamine, N-phenyl-N'-isopropyl-p-phenylenediamine, 4-hydroxydiphenylamine, aminophenol, and the like; sulfur-containing compounds such as phenothiazine, methylene blue, 2-mercaptobenzoimidazole, and the like; imides such as N-hydroxyphthalimide, and the like; oximes such as cyclohexaneoxime, p-quinonedioxime and the like; dialkylthiodipropionate; etc. The amount of the polymerization inhibitor is 0.001 to 10 parts by weight, preferably 0.01 to 1 part by weight, with respect to 100 parts by weight of the (meth) acrylic acid.

In the case where a phenol-based and/or quinone-based polymerization inhibitor is used in the dehydration esterification reaction, it is preferable to allow the reaction to proceed while blowing oxygen-containing gas such as air or the like in order to improve the polymerization inhibition effect. The concentration of oxygen in the gas is preferably 0.05 to 10% by volume for improving the polymerization inhibition effect and for keeping the gas at the explosion limit or less. As gas for dilution, it is common to use inert gas such as nitrogen, helium, argon or the like.

The amount of prepared gas is 0.005 to 0.3 L/min., preferably 0.01 to 0.1 L/min., with respect to 1 mol of the adamantanol as a material. When the amount of the prepared gas is smaller than such a range, the polymerization inhibition effect is not sufficient; and even when the prepared gas is blown in an amount larger than such a range, the effect is not changed.

After the dehydration esterification reaction is finished, it is preferable to remove the acid catalyst and the unreacted (meth)acrylic acid by washing the reaction solution with an alkali substance. A preferable alkaline washing solution is an aqueous solution which is not compatible with the reaction solution. Examples of such an alkaline aqueous solution include sodium hydroxide, potassium hydroxide, sodium carbonate, sodium hydrogencarbonate, ammonium hydroxide, tetraalkylammoniumhydroxides such as tetramethylammoniumhydroxide, and the like. The concentration thereof is preferably in the range of 1 to 25% by weight, pH may be 8 to 13.5, and the washing temperature may be in the range of 10 to 80° C. The amount of the alkaline aqueous solution to be used for one cycle of washing is preferably in the range of 0.1 to 1 part by weight with respect to 1 part by weight of the reaction solution. In the case where the washing with an alkaline substance is repeated twice or more, the concentration of the alkaline substance in the aqueous solution or the amount of the alkaline aqueous solution may be changed step by step. There is no specific limitation on the washing method as long as the reaction solution and the alkaline aqueous solution contact each other with a high efficiency. For example, in the case of the batch system, mixing by a stirrer is usable; and in the case of the continuous system, mixing by distribution to a static mixer or distribution to a pump combined with a mixing device is usable. The contact time, temperature, number of times of washing may be optionally selected in accordance with the intended quality.

By performing washing with water once or twice after the washing with an alkaline substance, the alkaline components residual in the reaction solution can be removed. In this case, it is preferable to remove ionic impurities as much as possible from the water to be used for the washing. Specifically, water having an electric conductivity of 10 mS/m or less is usable, for example. The amount of the water to be used for the washing is in the range of 0.1 to 1 part by weight with respect to 1 part by weight of the reaction solution. There is no specific limitation on the method of washing with water as long as the reaction solution and the water contact each other with a high efficiency, like in the case of the washing with an alkaline substance. Similarly, the conditions for the washing with water may be optionally changed.

After the washing with an alkaline substance, or the washing with water performed after the washing with an alkaline substance, washing with an acidic substance may be performed in order to remove metallic impurities. Acids which can be added are water-soluble acids including organic acids such as formic acid, acetic acid, propionic acid, oxalic acid, and the like; and inorganic acids such as hydrochloric acid, sulfuric acid, nitric acid, phosphoric acid, and the like. In consideration of separability from the reaction solution, it is preferable to use an inorganic acid. The concentration of the acidic substance is preferably in the range of 0.1 to 25% by weight, more preferably in the range of 0.5 to 5% by weight. Like in the case of the washing with an alkaline substance, the washing may be performed at a temperature in the range of 10 to 80° C. The amount of the acidic aqueous solution for one cycle of washing is preferably in the range of 0.1 to 1 part by weight with respect to 1 part by weight of the reaction solution. In the case where the washing with an acidic substance is repeated twice or more, the concentration of the acidic substance in the aqueous solution or the amount of the acidic aqueous solution may be changed step by step. The washing method and conditions may be optionally selected, like in the case of the washing with an alkaline substance.

By performing washing with water once or twice after the washing with an acidic substance, the acidic components residual in the reaction solution can be removed. In this case, ionic impurities need to be removed as much as possible from the water to be used for the washing. Specifically, it is preferable to use water having an electric conductivity of 10 mS/m or less. The amount of the water to be used for the washing is in the range of 0.1 to 1 part by weight with respect to 1 part by weight of the reaction solution. There is no specific limitation on the method of washing with water as long as the reaction solution and the water contact each other with a high efficiency, like in the case of the washing with an alkaline substance. The conditions for the washing with water may be optionally changed.

According to the present invention, it is preferable to perform precise filtration after the washing because the precise filtration can decrease the amount of the homopolymer or oligomer generated during the dehydration esterification reaction, and also can decrease the formazin standard turbidity by a certain degree. In this specification, the "precise filtration" means filtration performed by use of a filter having a pore diameter of 1.0 μm or less. Filtration methods include natural filtration, vacuum filtration, pressure filtration, and the like. Any of these is usable, but vacuum filtration or pressure filtration is usually preferable in order to perform the filtration efficiently. The pore diameter is preferably 0.1 to 1.0 p.m. According to the present invention, it is especially preferable to perform the precise filtration with a Teflon® filter having a pore diameter of 0.1 μm.

In order to take out the adamantyl (meth)acrylate, which is the target substance, in the form of crystal from the obtained reaction solution, a concentration operation is performed. The concentration operation may be performed by use of a vertical type concentration tank, a horizontal type concentration tank, a rotary evaporator type concentration tank or the like. The temperature for the concentration operation is in the range of 10 to 60° C., preferably in the range of 30 to 60° C. When the concentration temperature is higher than 60° C., the amount of generated polymer is increased. When the concentration temperature is lower than 10° C., the temperature of the condenser needs to be further decreased, which is not efficient. There is no specific limitation on the pressure at the time of concentration as long as the temperature is in the range of 10 to 60° C. The concentration operation may be performed in either an increased pressure system, a normal pressure system or a reduced pressure system. The reduced pressure system is usually preferable because the concentration operation can be performed efficiently in the reduced pressure system. In the case where the reduced pressure system is used, there is no specific limitation on the pressure, and the pressure may be optionally determined in consideration of the type of the solvent to be removed by distillation and the capability of the concentration device. The termination point of the concentration varies in accordance with the properties of the target substance, the concentration method, and the device to be used, and thus needs to be appropriately selected in accordance with the usage. The concentration of the adamantyl (meth)acrylate contained in the post-concentration reaction solution is in the range of 30 to 70%, preferably in the range of 40 to 65%.

It is preferable to perform the concentration operation while the polymerization inhibitor and the oxygen-containing gas as described above are blown, in order to decrease the formazin standard turbidity. Suppressing the generation of a homopolymer and an oligomer during the concentration step is important in order to obtain an adamantyl (meth)acrylate having a low formazin standard turbidity as a final product. There is no specific limitation on the method for blowing oxygen-containing gas as long as the gas can be supplied to the solution without the solution flowing in the opposite direction in the blowing tube. Usable methods include: a method of introducing a blowing tube from an upper mirror into the tank and blowing the gas; a method of blowing gas from a side surface of the tank; and a method of blowing gas from a lower solution discharge opening. In the case where a stirrer-equipped tank is used for the concentration operation, the concentration operation is mostly performed while stirring. Therefore, in the case where the blowing tube is inserted, the blowing tube needs to be sufficiently strong against the flow of the solution caused by the stirring.

In the case where the post-concentration adamantyl (meth)acrylate is crystalline, the solution containing the adamantyl (meth)acrylate may be provided as it is. Alternatively, a known method of, for example, performing crystallization by adding a poor solvent or controlling the cooling temperature without adding any solvent may be used to separate the crystal. Herein, the "poor solvent" is a solvent in which the solubility of the adamantyl (meth)acrylate represented by formula (1) is 5% or less at the crystallization temperature and which is uniform with the reaction solvent. There is no specific limitation on the type of the poor solvent. Examples of the poor solvent include aliphatic hydrocarbons such as hexane, heptane, octane, nonane, decane, cyclohexane, and the like; aromatic hydrocarbons such as benzene, toluene, xylene, and the like; esters such as ethyl acetate, propyl acetate, isopropyl acetate, butyl acetate, isobutyl acetate, and the like; etc. After the crystallization, wet crystal can be taken out by solid-liquid separation. When necessary, the wet crystal can be rinsed by use of a poor solvent or a mixed solvent of a poor solvent and another solvent to remove unnecessary components contained in the wet crystal and thus to improve the crystal purity. The poor solvent or any other solvent used for rinsing may be the poor solvent used for the crystallization, the reaction solvent or any other solvent. In accordance with the usage of the target substance, the adamantyl (meth)acrylate obtained by the crystallization may be dissolved in the solvent again, so that recrystallization by which concentration and/or crystallization is repeated may be performed.

In the case where the concentration step is included for the recrystallization, it is preferable to perform the above-described concentration operation in repetition. The object of the recrystallization is to increase the purity of the adamantyl (meth)acrylate. The purity of the adamantyl (meth)acrylate obtained as a final product is preferably 95% or higher, more preferably 98% or higher. It is possible to obtain an adamantyl (meth)acrylate having a purity of 99% or higher by repeating the recrystallization, but the optimal number of times of crystallization is preferably determined based on the amount of the solvent to be used and the purity. There is no specific limitation on the method of drying the post-crystallization adamantyl (meth)acrylate as long as the total content of the solvent and the moisture is 5% or less. As the drying method, a known method such as air-drying, vacuum drying or the like is usable.

According to the present invention, during the dehydration esterification reaction and also during the refinement, oxygen-containing gas is constantly blown in the presence of a phenol-based and/or quinone-based polymerization inhibitor. Owing to this, an adamantyl (meth)acrylate represented by formula (1) having a formazin standard turbidity of less than 1.7 NTU can be obtained. Prepared gas to be used with a phenol-based and/or quinone-based polymerization inhibitor preferably has an oxygen concentration in the range of 0.05 to 10.0% by volume. When the oxygen concentration is lower than such a range, the polymerization inhibition effect is not sufficient; whereas when the oxygen concentration is higher than such a range, the lower explosion limit of the organic solvent used may be exceeded, which increases the level of danger. Even when the prepared gas is blown in an amount exceeding 10.0% by volume, the polymerization inhibition effect is not changed. The prepared gas may be supplied to an organic phase to be concentrated in a batch system or a continuous system. The method of supplying continuously is preferable because the oxygen concentration in the continuous system can be constantly controlled. Regarding the supply amount of the prepared gas in the case of the continuous supply, it is not necessary to set the lower limit because the polymerization inhibitor is sufficiently effective even in the presence of an extremely small amount of oxygen. However, the upper limit needs to be set in accordance with the production facilities because the gas needs to be used in an amount less than the above-described lower explosion limit, and also because in the case where the concentration operation is performed at a reduced pressure, the upper limit of the supply amount depends on the capability of the facilities such as a condenser, a vacuum pump or the like. The supply amount of the prepared gas is 0.005 to 0.3 L/min., preferably 0.01 to 0.1 L/min., with respect to 1 mol of the adamantyl (meth)acrylate. When the amount of the prepared gas is smaller than such a range, the polymerization inhibition effect is not sufficient; and even when the prepared gas is blown in an amount exceeding such a range, the polymerization inhibition effect is not changed.

A (meth)acrylic copolymer according to the present invention can be produced by copolymerizing an adamantyl (meth)acrylate represented by formula (1) and at least one compound selected form the group consisting of compounds represented by formula (3), formula (4), formula (5) and formula (6).

[Chemical Formula 8]

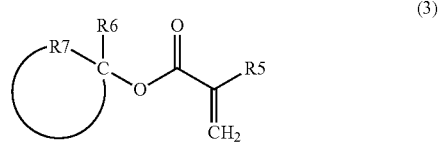

(3)

(In the formula, R5 represents hydrogen or a methyl group; R6 represents an alkyl group having a carbon number of 1 to 4; and R7 represents a cycloalkyl group or an alicyclic alkyl group having a carbon number of 5 to 20.)

[Chemical Formula 9]

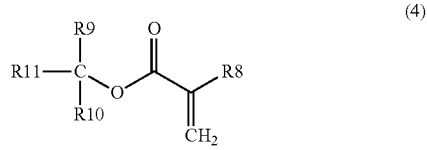

(4)

(In the formula, R8 represents hydrogen or a methyl group; R9 and R10 may be the same as, or different from each other, and each represent an alkyl group having a carbon number of 1 to 4; and R11 represents a cycloalkyl group or an alicyclic alkyl group having a carbon number of 5 to 20.)

[Chemical Formula 10]

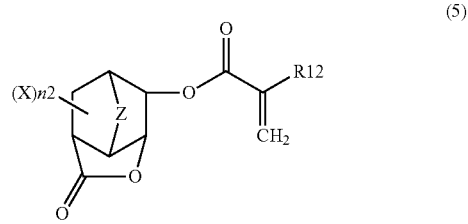

(5)

(In the formula, R12 represents hydrogen or a methyl group; Z represents methylene (—$CH_2$—) or oxa (—O—); Xs may be the same as, or different from, each other, and each represent a hydroxyl group, a halogen group, a nitrile group, a carboxylic acid group, an alkoxycarbonyl group having a carbon number of 1 to 4, or an alkoxide group having a carbon number of 1 to 4; and n2 represents an integer of 0 to 2.)

[Chemical Formula 11]

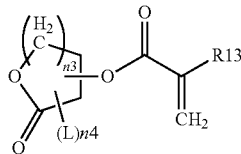

(6)

(In the formula, R13 represents hydrogen or a methyl group; n3 represents an integer of 1 to 3; L represents a methyl group, an ethyl group, a hydroxyl group, or a halogen group; and n4 represents an integer of 0 to 2.)

Compounds represented by formula (3) include 2-methyl-2-(meth)acryloyloxyadamantane, 2-ethyl-2-(meth)acryloyloxyadamantane, 2-isopropyl-2-(meth)acryloyloxyadamantane, 2-n-propyl-2-(meth)acryloyloxyadamantane, 2-n-butyl-2-(meth)acryloyloxyadamantane, 1-methyl-1-(meth)acryloyloxycyclopentane, 1-ethyl-1-(meth)acryloyloxycyclopentane, 1-methyl-1-(meth)acryloyloxycyclohexane, 1-ethyl-1-(meth)acryloyloxycyclohexane, 1-methyl-1-(meth)acryloyloxycycloheptane, 1-ethyl-1-(meth)acryloyloxycycloheptane, 1-methyl-1-(meth)acryloyloxycyclooctane, 1-ethyl-1-(meth)acryloyloxycyclooctane, 2-ethyl-2-(meth)acryloyloxydecahydro-1,4:5,8-dimethanonaphthalene, 2-ethyl-2-(meth)acryloyloxynorbornane, and the like.

Compounds represented by formula (4) include 2-cyclohexyl-2-(meth)acryloyloxypropane, 2-(4-methylcyclohexyl)-2-(meth)acryloyloxypropane, 2-adamantyl-2-(meth)acryloyloxypropane, 2-(3-(1-hydroxy-1-methylethyl)adamantyl)-2-(meth)acryloyloxypropane, and the like.

Compounds represented by formula (5) include 2-(meth)acryloyloxy-5-oxo-4-oxatricyclo[4.2.1.0$^{3,7}$]nonane, 7- or 8-(meth)acryloyloxy-3-oxo-4-oxatricyclo[5.2.1.0$^{2,6}$]decane, 9-(meth)acryloyloxy-3-oxo-2-oxa-6-oxatricyclo[4.2.1.0$^{4,8}$]nonane, 2-(meth)acryloyloxy-5-oxo-4-oxa-8-oxatricyclo[4.2.1.0$^{3,7}$]nonane, 2-(meth)acryloyloxy-9-methoxycarbonyl-5-oxo-4-oxatricyclo[4.2.1.0$^{3,7}$]nonane, 2-(meth)acryloyloxy-5-oxo-4-oxatricyclo[4.2.1.0$^{3,7}$]nonane-6-carbonitrile, and the like.

Compounds represented by formula (6) include α-(meth)acryloyloxy-γ-butyrolactone, β-(meth)acryloyloxy-γ-butyrolactone, (meth)acryloyloxypantolactone, and the like.

The copolymerization ratio of the compounds represented by formulas (1) and (3) through (6) is as follows. A compound represented by formula (1) is preferably contained at a content of 5 to 40% by weight as a repeating unit. At least one compound represented by formula (3) or (4) is preferably contained at a content of 20 to 50% by weight as a repeating unit. At least one compound represented by formula (5) or (6) is preferably contained at a content of 15 to 50% by weight as a repeating unit. (Note that the total sum of the copolymerization ratios of the compounds represented by formulas (1) and (3) through (6) is 100% by weight.)

Polymerization is generally performed as follows. The repeating unit is dissolved in a solvent, a catalyst is added, and the reaction is allowed to proceed while the substances are heated or cooled. The conditions of the polymerization reaction may be optionally set in accordance with the type of the initiator, heat, light or the like for starting polymerization, temperature, pressure, concentration, type of solvent, type(s) of additive(s) or the like. Polymerization of a (meth)acrylic copolymer according to the present invention can be performed by a known method, for example, radical polymerization using a radical generator such as azoisobutylonitrile, peroxide or the like, or ion polymerization using a catalyst such as alkyl lithium, a Grignard reagent or the like.

Solvents usable for the polymerization reaction of a (meth)acrylic copolymer according to the present invention include, for example, ketones such as 2-butanone, 2-heptanone, methylisobutylketone, cyclohexanone, and the like; alkanes such as hexane, heptane, octane, cyclohexane, cyclooctane, decalin, norbornane, and the like; alcohols such as methanol, ethanol, propanol, 2-propanol, n-butanol, sec-butanol, t-butanol, pentanol, hexanol, propyleneglycolmonomethylether, and the like; ethers such as diethylether, tetrahydrofuran, 1,4-dioxane, and the like; carboxylic acid esters such as ethyl acetate, butyl acetate, methyl lactate, propyleneglycolmonomethylether acetate, and the like. These solvents may be used independently or in a combination of two or more.

A (meth)acrylic copolymer obtained by the present invention may be refined by a known method. Specifically, metallic impurities can be removed by a combination of ultrafiltration, precise filtration, washing with an acidic substance, washing with water having an electric conductivity of 10 mS/m or less, and extraction. In the case where washing with an acidic substance is performed, acids which can be added are water-soluble acids including organic acids such as formic acid, acetic acid, propionic acid, and the like; and inorganic acids such as hydrochloric acid, sulfuric acid, nitric acid, phosphoric acid, and the like. In consideration of separability from the reaction solution, it is preferable to use an inorganic acid. Oligomers can be removed by a combination of ultrafiltration, precise filtration, crystallization, recrystallization, extraction, washing with water having an electric conductivity of 10 mS/m or less, and the like.

According to the present invention, as a resinous additive usable together with a (meth)acrylic copolymer, a photoacid generator, a surfactant, an acid diffusion suppressant, a sensitizer and the like may be optionally added in combination when necessary. Especially, the photoacid generator is indispensable for performing photolithography. Specific examples of the photoacid generator include triphenylphosphonium salt compounds, diphenyliodonium salt compounds, diphenylsulfonium salt compounds, alkylsulfonates, imide sulfonates, disulfonic acids, sulfonyldiazomethanes, and the like. The amount of the photoacid generator is 0.1 to 40 parts by weight, preferably 0.2 to 30 parts by weight, with respect to the (meth)acrylic copolymer.

The polystyrene-converted weight-average molecular weight of the (meth)acrylic copolymer measured by gel permeation chromatography (GPC) (hereinafter, referred to as the "Mw") is preferably 1,000 to 500,000, more preferably 3,000 to 100,000. The ratio, of the (meth)acrylic copolymer, of Mw with respect to the polystyrene-converted number-average molecular weight measured by GPC (hereinafter, referred to as the "Mn"), namely, Mw/Mn, is usually 1 to 10, preferably 1 to 5. According to the present invention, the (meth)acrylic copolymers can be used independently or in a mixture of two or more.

EXAMPLES

Hereinafter, the present invention will be specifically described by way of examples, but the present invention is not limited to the following examples. In the examples, the purity of the (meth)acrylic monomer and the amount of the polymerization inhibitor were measured by gas chromatography, the residual metal was quantified by ICP-MS, and the polymer was evaluated by GPC. The turbidity was measured by a turbidimeter Type 2100P (produced by Central Kagaku Corp.) after 10 parts by weight of (meth)acrylic monomer was dissolved in 100 parts by weight of methylethylketone or tetrahydrofuran used for the polymerization. The turbidity was measured on the basis of the formazin standard solution. A StablCal® standard solution (<0.1 NTU, 20 NTU, 100 NTU, 800 NTU) was used for creating a calibration curve, and the calibration curve was used for evaluation.

Example 1

Synthesis of 3-hydroxy-1-adamantyl methacrylate

To a 2 L jacket-equipped separable flask provided with a stirrer, a thermometer, a Dean-Stark water separator, a Dimroth condenser and a gas blowing tube, 84.0 g of 1,3-adamantanediol, 124.1 g of methacrylic acid, 0.38 g of p-methoxyphenol as a polymerization inhibitor, 1.2 g of concentrated sulfuric acid as an acid catalyst, and 750 ml of toluene as a solvent were put. Prepared gas diluted with nitrogen so as to have an oxygen concentration of about 5% by volume was supplied at a rate of 0.2 L/min. The reaction operation was performed as follows. While the solution was heated and water generated as a secondary product was removed by the Dean-Stark water separator, the reflux state was continued for 5 hours. Thus, a reaction solution containing 3-hydroxy-1-adamantyl methacrylate was obtained. The obtained reaction solution was cooled down to room temperature, and then a 10% by weight of aqueous solution of sodium hydroxide was added while stirring to neutralize the residual methacrylic acid and sulfuric acid. Then, the neutralized water phase was drawn out from the two-phase solution. To the residual organic phase, 0.85 g of p-methoxyphenol was added as a polymerization inhibitor. The resultant solution was washed with 5% by weight of dilute sulfuric acid and with 500 ml of ion exchange water, twice for each. After the washing, precise filtration was performed by use of a Teflon® filter having a pore diameter of 0.1 μm. Then, concentration-crystallization was performed by use of an evaporator while the temperature of the solution was kept at 40° C., until the weight of the solution became 110 g. After the concentration was finished, cooling crystallization was performed at a temperature of an ice water bath to separate the crystal by filtration. The crystal was rinsed with heptane twice, and then dried at a reduced pressure at 35° C. for 24 hours. During the process from the dehydration esterification reaction to the solid-liquid separation and until the termination of rinsing performed by use of ion exchange water, the prepared gas was kept blown into the solution. Table 1 shows the analysis results of the obtained 3-hydroxy-1-adamantyl methacrylate. Methylethylketone was used as the solvent for measuring the turbidity.

Comparative Example 1-1

Synthesis of 3-hydroxy-1-adamantyl methacrylate 3-hydroxy-1-adamantyl methacrylate was synthesized under the same conditions as those of Example 1 except that the prepared gas was not blown in the refinement step, which was post-treatment step performed after the dehydration esterification reaction. In the post-treatment step, filtration with a 5A filter (having a pore diameter of 7 μm) was performed instead of precise filtration. Table 1 shows the analysis results of the obtained 3-hydroxy-1-adamantyl methacrylate.

Comparative Example 1-2

Synthesis of 3-hydroxy-1-adamantyl methacrylate 3-hydroxy-1-adamantyl methacrylate was synthesized under the same conditions as those of Example 1 except that the prepared gas was not blown in the refinement step, which was post-treatment step performed after the dehydration esterification reaction, although precise filtration was performed. Table 1 shows the analysis results of the obtained 3-hydroxy-1-adamantyl methacrylate.

Example 2

Synthesis of 3,5-dihydroxy-1-adamantyl methacrylate

To a 2 L jacket-equipped separable flask provided with a stirrer, a thermometer, a Dean-Stark water separator, a Dimroth condenser and a prepared gas introduction tube, 128.9 g of 1,3,5-adamantanetriol, 361 g of methacrylic acid, 1.7 g of concentrated sulfuric acid as an acid catalyst, 1.1 g of p-methoxyphenol as a polymerization inhibitor, and 750 ml of toluene as a solvent were put. Prepared gas diluted with nitrogen so as to have an oxygen concentration of about 5% by volume was supplied at a rate of 0.2 L/min. The reaction operation was performed as follows. While the solution was heated and water generated as a secondary product was removed by the Dean-Stark water separator, the reflux state was continued for 12 hours. Thus, 3,5-dihydroxy-1-adamantyl methacrylate was synthesized. The obtained reaction solution was cooled down to room temperature, and then a 10% by weight of aqueous solution of sodium hydroxide was added while stirring to neutralize the residual methacrylic acid and sulfuric acid. Then, the neutralized water phase was drawn out from the two-phase solution. The resultant organic phase was washed with 500 ml of ion exchange water twice. After the water phase was all united, extraction was performed with 300 ml of ethyl acetate twice. To the ethyl acetate solution, 0.76 g of p-methoxyphenol was added as a polymerization inhibitor and dissolved completely. Precise filtration was performed by use of a Teflon® filter having a pore diameter of 0.1 μm. Then, the resultant solution was concentrated by use of an evaporator while the temperature of the solution was kept at 40° C., until the weight of the solution became 110 g. After the concentration was finished, cooling crystallization was performed at a temperature of an ice water bath to separate the crystal by filtration. The crystal was rinsed with ion exchange water twice, and then dried at a reduced pressure at 35° C. for 24 hours. During the process from the dehydration esterification reaction to the solid-liquid separation and until the termination of rinsing performed by use of ion exchange water, the prepared gas was kept blown into the solution. Table 1 shows the analysis results of the obtained 3,5-dihydroxy-1-adamantyl methacrylate. Tetrahydrofuran was used as the solvent for measuring the turbidity.

Comparative Example 2

Synthesis of 3,5-dihydroxy-1-adamantyl methacrylate 3,5-dihydroxy-1-adamantyl methacrylate was synthesized under the same conditions as those of Example 2 except that the prepared gas was not blown in the refinement step, which was post-treatment step performed after the dehydration esterification reaction. In the post-treatment step, filtration with a 5A filter (having a pore diameter of 7 μm) was performed instead of precise filtration. Table 1 shows the analysis results of the obtained 3,5-dihydroxy-1-adamantyl methacrylate.

Example 3

Synthesis of 3-hydroxy-1-adamantyl acrylate

To a 2 L jacket-equipped separable flask provided with a stirrer, a thermometer, a Dean-Stark water separator, a Dimroth condenser and a prepared gas introduction tube, 84 g of 1,3-adamantanediol, 108 g of acrylic acid, 0.76 g of p-methoxyphenol as a polymerization inhibitor, 1.3 g of concentrated sulfuric acid as an acid catalyst, and 750 ml of toluene as a solvent were put. Prepared gas diluted with nitrogen so as to have an oxygen concentration of about 5% by volume was supplied at a rate of 0.2 L/min. The reaction operation was performed as follows. While the solution was heated and water generated as a secondary product was removed by the Dean-Stark water separator, the reflux state was continued for 6 hours. Thus, 3-hydroxy-1-adamantyl acrylate was synthesized. The obtained reaction solution was cooled down to room temperature, and then a 10% by weight of aqueous solution of sodium hydroxide was added while stirring to neutralize the residual acrylic acid and sulfuric acid. Then, the neutralized water phase was drawn out from the two-phase solution. To the residual organic phase, 0.85 g of p-methoxyphenol was added as a polymerization inhibitor. The resultant solution was washed with 5% by weight of dilute sulfuric acid and with 500 ml of ion exchange water, twice for each. After the washing, precise filtration was performed by use of a Teflon® filter having a pore diameter of 0.1 μm. Then, cooling crystallization was performed at a temperature of an ice water bath to separate the crystal by filtration. The crystal was rinsed with heptane twice, and then dried at a reduced pressure at 25° C. for 24 hours. During the process from the dehydration esterification reaction to the solid-liquid separation and until the termination of rinsing performed by use of ion exchange water, the prepared gas was kept blown into the solution. Table 1 shows the analysis results of the obtained 3-hydroxy-1-adamantyl acrylate. Methylethylketone was used as the solvent for measuring the turbidity.

Comparative Example 3

Synthesis of 3-hydroxy-1-adamantyl acrylate 3-hydroxy-1-adamantyl acrylate was synthesized under the same conditions as those of Example 3 except that the prepared gas was not blown in the refinement step, which was post-treatment step performed after the dehydration esterification reaction. In the post-treatment step, filtration with a 5A filter (having a pore diameter of 7 μm) was performed instead of precise filtration. Table 1 shows the analysis results of the obtained 3-hydroxy-1-adamantyl acrylate.

TABLE 1

|  | Compound | GC purity (%) | Polymerization inhibitor (ppm) | Metal *1 (ppb) | Oligomer (ppm) | Turbidity (NTU) |
|---|---|---|---|---|---|---|
| Example 1 | 3-hydroxy-1-adamantyl methacrylate | 99.9 | <50 | <30 | 700 | 0.1 |
| Comparative Example 1-1 | same as above | 99.8 | <50 | <30 | 1100 | 2.7 |
| Comparative Example 1-2 | same as above | 99.9 | <50 | <30 | 800 | 2.0 |
| Example 2 | 3,5-dihydroxy-1-adamantyl methacrylate | 99.5 | <50 | <30 | 1600 | 0.1 |
| Comparative Example 2 | same as above | 99.2 | <50 | <30 | 1700 | 1.7 |
| Example 3 | 3-hydroxy-1-adamantyl acrylate | 99.9 | <50 | <30 | 2500 | 0.1 |
| Comparative Example 3 | same as above | 99.9 | <50 | <30 | 2900 | 4.9 |

*1: Measured for 12 types of metal materials of Li, Na, Al, K, Fe, Cr, Ni, Mn, Cu, Mg, Sn and Pb.

Example 4

Synthesis of Copolymer A 3.19 g of 3-hydroxy-1-adamantyl methacrylate having a turbidity of 0.1 NTU synthesized in Example 1 as the compound represented by formula (1), 3.37 g of 2-ethyl-2-methacryloyloxyadamantane as the compound represented by formula (3), 3.99 g of 2-methacryloyloxy-5-oxo-4-oxatricyclo[4.2.1.0$^{3,7}$]nonane as the compound represented by formula (5), and 0.40 g of azobisisobutylonitrile were dissolved in 90 mL of tetrahydrofuran and polymerized for 21 hours under a nitrogen atmosphere while the reaction temperature was kept at 58° C. After the polymerization, the reaction solution was dropped into 450 mL of n-hexane to solidify and refine the generated resin, and the generated white powder was filtrated and dried overnight at 40° C. at a reduced pressure. Thus, (meth)acrylic copolymer A was obtained.

Comparative Example 4

The same operation was performed as that of Example 4 except that 3-hydroxy-1-adamantyl methacrylate having a turbidity of 2.7 NTU synthesized in Comparative Example 1-1 was used as the compound represented by formula (1). Thus, (meth)acrylic copolymer B was obtained.

Example 5

3.41 g of 3,5-dihydroxy-1-adamantyl methacrylate having a turbidity of 0.1 NTU synthesized in Example 2 as the compound represented by formula (1), 3.33 g of 2-ethyl-2-methacryloyloxyadamantane as the compound represented by formula (3), 4.00 g of 2-methacryloyloxy-5-oxo-4-oxatricyclo[4.2.1.0$^{3,7}$]nonane as the compound represented by formula (5), and 0.41 g of azobisisobutylonitrile were dissolved in 90 mL of tetrahydrofuran and polymerized for 21 hours under a nitrogen atmosphere while the reaction temperature was kept at 60° C. After the polymerization, the reaction solution was dropped into 450 mL of n-hexane to solidify and refine the generated resin, and the generated white powder was filtrated and dried overnight at 40° C. at a reduced pressure. Thus, (meth)acrylic copolymer C was obtained.

Comparative Example 5

The same operation was performed as that of Example 5 except that 3,5-dihydroxy-1-adamantyl methacrylate having a turbidity of 1.7 NTU synthesized in Comparative Example 2 was used as the compound represented by formula (1). Thus, (meth)acrylic copolymer D was obtained.

Example 6

3.00 g of 3-hydroxy-1-adamantyl acrylate having a turbidity of 0.1 NTU synthesized of Example 3 as the compound represented by formula (1), 3.36 g of 2-ethyl-2-methacryloyloxyadamantane as the compound represented by formula (3), 3.98 g of 2-methacryloyloxy-5-oxo-4-oxatricyclo[4.2.1.0$^{3,7}$]nonane as the compound represented by formula (5), and 0.41 g of azobisisobutylonitrile were dissolved in 90 mL of tetrahydrofuran and polymerized for 23 hours under a nitrogen atmosphere while the reaction temperature was kept at 57° C. After the polymerization, the reaction solution was dropped into 450 mL of n-hexane to solidify and refine the generated resin, and the generated white powder was filtrated and dried overnight at 40° C. at a reduced pressure. Thus, (meth)acrylic copolymer E was obtained.

Comparative Example 6

The same operation was performed as that of Example 6 except that 3-hydroxy-1-adamantyl acrylate having a turbidity of 4.9 NTU synthesized in Comparative Example 3 was used as the (meth)acrylic monomer represented by formula (1). Thus, (meth)acrylic copolymer F was obtained.

The obtained six types of (meth)acrylic copolymers were each treated as follows. 100 parts by weight of each of copolymers A, B, E and F, 10 parts by weight of triphenylsulfonium-nonafluorobutanesulfonate (TPS-109 produced by Midori Kagaku Co., Ltd.), and propyleneglycolmonomethylacetate were mixed together. 100 parts by weight of each of copolymers C and D, 10 parts by weight of triphenylsulfoniumnonafluorobutanesulfonate (TPS-109 produced by Midori Kagaku Co., Ltd.), and ethyl lactate were mixed together. Thus, resin compositions for photoresist having a copolymer concentration of 6.3% by weight were prepared. After an anti-reflective coating (ARC-29 produced by Nissan Chemical Industries, Ltd.) was spin-coated on a silicon wafer, each of the resin compositions for photoresist was spin-coated on the anti-reflective coating to form a photosensitive layer having a thickness of 100 nm. After being prebaked on a hot plate at a temperature of 90° C. for 60 seconds, the photosensitive layer was irradiated with electron beams of a 100 nm half-pitch line-and-space pattern (10 lines) by an electron beam lithography system (ELS-7700 produced by Elionix Inc.), and then was post-exposure baked (PEB) at a predetermined temperature for 90 seconds. Then, the photosensitive layer was developed by use of 0.3 M aqueous solution of tetramethylammonium hydroxide for 60 seconds and rinsed with pure water to obtain a line-and-space pattern. The results are shown in Table 2. The obtained line-and-space pattern was observed with an FE-SEM, and the resolution and the line edge roughness (LER) were measured. The results are shown in Table 2. It was found that when compared at the same PEB temperature and the same exposure amount, the (meth)acrylic copolymers produced using a (meth)acrylic monomer having a low turbidity show an equivalent or slightly better LER and a better resolution. It was also found that especially the compounds containing two hydroxyl groups show a significantly better resolution.

TABLE 2

|  | Copolymer | Compound | PEB temperature (° C.) | Exposure amount (μC/cm$^2$) | Resolution (nm) | LER (nm) |
| --- | --- | --- | --- | --- | --- | --- |
| Example 4 | A | 3-hydroxy-1-adamantyl methacrylate | 110 | 70 | 115.2 | 9.0 |
| Comparative Example 4 | B | same as above | same as above | same as above | 118.3 | 9.0 |
| Example 5 | C | 3,5-dihydroxy-1-adamantyl methacrylate | 100 | 80 | 80.3 | 9.6 |
| Comparative Example 5 | D | same as above | same as above | same as above | 97.5 | 9.8 |
| Example 6 | E | 3-hydroxy-1-adamantyl acrylate | 90 | 100 | 88.1 | 7.8 |
| Comparative Example 6 | F | same as above | same as above | same as above | 89.2 | 8.2 |

INDUSTRIAL APPLICABILITY

The present invention is usable for a photolithography process during production of a semiconductor device using an ArF excimer laser lithography.

The invention claimed is:

1. An adamantyl (meth)acrylate represented by formula (1), having a formazin standard turbidity of less than 1.7 NTU when being dissolved or diluted in methylethylketone or tetrahydrofuran:

(1)

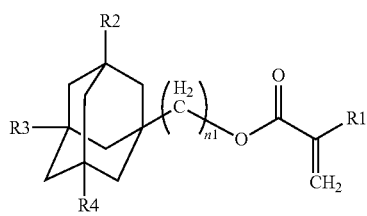

wherein in the formula, R1 represents hydrogen or a methyl group; R2 through R4 each independently represent a hydrogen atom, a hydroxyl group, an alkyl group having a carbon number of 1 to 3, an aryl group, an alkoxy group, an aryloxy group, a halogen group, an alkyl halide group, or a hydroxyalkyl group; and n1 represents 0 or 1.

2. The adamantyl (meth)acrylate according to claim 1, which is selected from the group consisting of 1-adamantyl (meth)acrylate, 3-hydroxy-1-adamantyl (meth)acrylate, 3,5-dihydroxy-1-adamantyl (meth)acrylate, 3,5,7-trihydroxy-1-adamantyl (meth)acrylate, 3,5-dimethyl-1-adamantyl (meth)acrylate, 5,7-dimethyl-3-hydroxy-1-adamantyl (meth)acrylate, 5-methoxy-3-hydroxy-1-adamantyl (meth)acrylate, 5-ethoxy-3-hydroxy-1-adamantyl (meth)acrylate, (meth)acryloyloxy-(1-adamantyl)methane, and (meth)acryloyloxy-(1-(3-hydroxymethyl)adamantyl)methane.

3. A polymer, comprising the adamantyl (meth)acrylate according to claim 1 as a repeating unit.

4. A method for producing the adamantyl (meth)acrylate according to claim 1, the method comprising the steps of:
causing a dehydration esterification reaction of an adamantanol represented by formula (2) and a (meth)acrylic acid in the presence of an acid catalyst; and
performing refinement while supplying oxygen-containing gas in the presence of a phenol-based and/or quinone-based polymerization inhibitor in post-treatment performed after the dehydration esterification reaction:

(2)

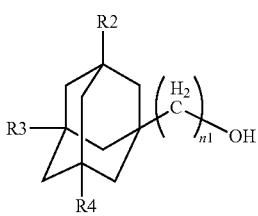

wherein in the formula, R2 through R4 may be the same as, or different from each other, and each represent a hydrogen atom, a hydroxyl group, an alkyl group having a carbon number of 1 to 3, an aryl group, an alkoxy group, an aryloxy group, a halogen group, an alkyl halide group, or a hydroxyalkyl group; and n1 represents 0 or 1, and
wherein oxygen-containing gas is constantly blown in the refinement step and also in the dehydration esterification reaction and
the gas used in performing the refinement and esterification reaction has an oxygen concentration of 0.05 to 10% by volume, and is supplied in an amount of 0.005 to 0.3 L/min. with respect to 1 mol of the adamantanol.

5. A method for producing the adamantyl (meth)acrylate according to claim 1 the method comprising:
causing a dehydration esterification reaction of an adamantanol represented by formula (2) and a (meth)acrylic acid in the presence of an acid catalyst;
performing refinement while supplying oxygen-containing gas in the presence of a phenol-based and/or quinone-based polymerization inhibitor in post-treatment performed after the dehydration esterification reaction:

(2)

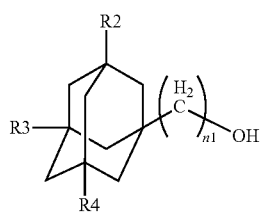

wherein in the formula, R2 through R4 may be the same as, or different from each other, and each represent a hydrogen atom, a hydroxyl group, an alkyl group having a carbon number of 1 to 3, an aryl group, an alkoxy group, an aryloxy group, a halogen group, an alkyl halide group, or a hydroxyalkyl group; and n1 represents 0 or 1, and
wherein oxygen-containing gas is constantly blown in the refinement step and also in the dehydration esterification reaction; and
performing precise filtration in the post-treatment performed after the dehydration esterification reaction.

6. The method according to claim 4, wherein the adamantyl (meth)acrylate is selected from the group consisting of 1-adamantyl (meth)acrylate, 3-hydroxy-1-adamantyl (meth)acrylate, 3,5-dihydroxy-1-adamantyl (meth)acrylate, 3,5,7-trihydroxy-1-adamantyl (meth)acrylate, 3,5-dimethyl-1-adamantyl (meth)acrylate, 5,7-dimethyl-3-hydroxy-1-adamantyl (meth)acrylate, 5-methoxy-3-hydroxy-1-adamantyl (meth)acrylate, 5-ethoxy-3-hydroxy-1-adamantyl (meth)acrylate, (meth)acryloyloxy-(1-adamantyl)methane, and (meth)acryloyloxy-(1-(3-hydroxymethyl)adamantyl) methane.

7. A (meth)acrylic copolymer obtained as a result of copolymerization of the adamantyl (meth)acrylate according to claim 1 and at least one compound selected from the group consisting of compounds represented by formula (3), formula (4), formula (5) and formula (6), wherein the adamantyl (meth)acrylate is contained at a content of 5 to 40% by weight:

(3)

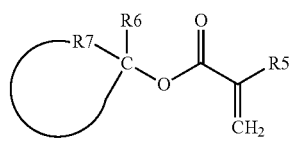

wherein in the formula, R5 represents hydrogen or a methyl group; R6 represents an alkyl group having a carbon number of 1 to 4; and R7 represents a cycloalkyl group or an alicyclic alkyl group having a carbon number of 5 to 20;

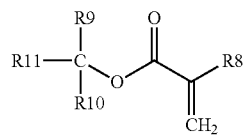
(4)

wherein in the formula, R8 represents hydrogen or a methyl group; R9 and R10 may be the same as, or different from each other, and each represent an alkyl group having a carbon number of 1 to 4; and R11 represents a cycloalkyl group or an alicyclic alkyl group having a carbon number of 5 to 20;

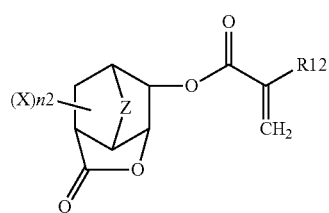
(5)

wherein in the formula, R12 represents hydrogen or a methyl group; Z represents methylene (—$CH_2$—) or oxa (—O—); Xs may be the same as, or different from, each other, and each represent a hydroxyl group, a halogen group, a nitrile group, a carboxylic acid group, or an alkoxycarbonyl group having a carbon number of 1 to 4, or an alkoxide group having a carbon number of 1 to 4; and n2 represents an integer of 0 to 2; and

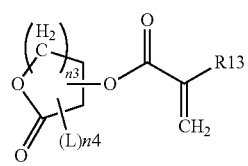
(6)

wherein in the formula, R13 represents hydrogen or a methyl group; n3 represents an integer of 1 to 3; L represents a methyl group, an ethyl group, a hydroxyl group, or a halogen group; and n4 represents an integer of 0 to 2.

8. A method for producing the adamantyl (meth)acrylate according to claim 1, the method comprising:

causing a dehydration esterification reaction of an adamantanol represented by formula (2) and a meth(acrylic) acid in the presence of an acid catalyst; and performing refinement while supplying oxygen-containing gas in the presence of a phenol based and/or quinone-based polymerization inhibitor in post-treatment performed after the dehydration esterification reaction;

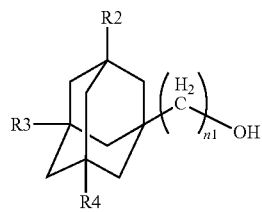
(2)

wherein in the formula, R2 through R4 may be the same as or different from each other and each represents a hydrogen atom, a hydroxyl group, an alkyl group having a carbon number of 1 to 3, an aryl group, an alkoxy group, an aryloxy group, a halogen group, an alkyl halide group, or a hydroxyalkyl group and n1 represents 0 or 1, and wherein the method further comprises performing precise filtration in the post-treatment performed after the dehydration esterification reaction.

* * * * *